United States Patent
Balekhov et al.

(10) Patent No.: US 8,431,616 B2
(45) Date of Patent: Apr. 30, 2013

(54) METHOD FOR PRODUCING A DISINFECTING AGENT

(75) Inventors: Sergei Alexeevich Balekhov, Moscow (RU); Valery Mikhailovich Nikolaev, Moscow (RU); Alexei Semenovich Scherba, Moscow (RU)

(73) Assignee: Sergei Alexeevich Balekhov, Moscow (RU)

( * ) Notice: Subject to any disclaimer, the term of this patent is extended or adjusted under 35 U.S.C. 154(b) by 1110 days.

(21) Appl. No.: 12/084,594

(22) PCT Filed: Nov. 14, 2005

(86) PCT No.: PCT/RU2005/000563
§ 371 (c)(1),
(2), (4) Date: May 30, 2008

(87) PCT Pub. No.: WO2007/053053
PCT Pub. Date: May 10, 2007

(65) Prior Publication Data
US 2009/0275663 A1    Nov. 5, 2009

(30) Foreign Application Priority Data
Nov. 7, 2005  (RU) .................................. 2005134224

(51) Int. Cl.
*A61K 31/155* (2006.01)
(52) U.S. Cl.
USPC .......................................... 514/634; 514/635
(58) Field of Classification Search .................. 514/634, 514/635
See application file for complete search history.

(56) References Cited

U.S. PATENT DOCUMENTS

| | | | |
|---|---|---|---|
| 2,830,006 A | 4/1958 | Birtwell et al. | |
| 4,725,623 A | 2/1988 | Whitekettle et al. | |
| 4,725,624 A | 2/1988 | Whitekettle et al. | |
| 6,031,119 A * | 2/2000 | Lee et al. .................... | 556/410 |
| 6,296,744 B1 | 10/2001 | Djeiranishvili et al. | |
| 2004/0220275 A1* | 11/2004 | Lutzeler et al. ............. | 514/642 |

FOREIGN PATENT DOCUMENTS

| | | |
|---|---|---|
| RU | 2 119 802 | 10/1998 |
| RU | 2 147 032 | 3/2000 |

OTHER PUBLICATIONS

International Search Report.
International Search Report 2008.

* cited by examiner

*Primary Examiner* — Paul Zarek
(74) *Attorney, Agent, or Firm* — Collard & Roe, P.C.

(57) ABSTRACT

The invention relates to medicine, in particular to sanitary and hygiene, more specifically to methods for producing a disinfecting agent for decontaminating different types of water, including drinking water. The inventive disinfecting agent producing method by dissolving quaternary ammonium compounds in water in the presence of an active additive in the form of guanidines, consists in preparing an aqueous 1-15% guanidine solution by permanently agitating it at a temperature ranging from 30 to 90° C., in cooling the solution accompanied with a precipitation control, when the precipitation process is over, in filtering the solution by using a filter whose cell size ranges from 10 to 1 mkm and in adding the quaternary ammonium compounds into the solution in such away that the concentration thereof in said solution is equal to 0.1-3%.

5 Claims, No Drawings

METHOD FOR PRODUCING A DISINFECTING AGENT

CROSS REFERENCE TO RELATED APPLICATIONS

This application is the National Stage of PCT/RU2005/000563 filed on Nov. 14, 2005, which claims priority under 35 U.S.C. §119 of Russian Application No. 2005134224 filed on Nov. 7, 2005. The international application under PCT article 21(2) was not published in English.

This invention relates to medicine, in particular, to sanitation and hygiene, and more specifically, to methods for producing a disinfecting agent for disinfection purposes.

There is a prior art method that is used to produce a disinfecting agent by dissolving quaternary ammonium compounds in water (see: U.S. Pat. No. 4,725,623, C02F1/50, 1987).

The prior art method produces a strong disinfecting agent.

The method disclosed in the aforesaid U.S. patent is not satisfactory enough because it requires large quantities of quaternary ammonium compounds to be used to produce the desired disinfecting effect, which fact restricts the range of agent applications and complicates preparation of the solution because of the need to use dispensers and homogenizers.

In another prior art method for producing a disinfecting agent, quaternary ammonium compounds are dissolved in water in the presence of an active additive (see: U.S. Pat. No. 4,725,624, C02F1/50, 1987).

The method disclosed in this U.S. patent is the closest related prior art of the claimed invention in technical idea and result achieved, and for this reason it has been chosen as immediate prior art of this invention.

According to the prior art method, a reactor is filled with a quantity of water, and 2-bromo-2-nitropropane-1,3 diol is added to the water to prepare an aqueous solution of n-alkyl-dimethylbenzyl-ammonium chloride in the presence of the said active additive.

The prior art method is advantageous because it is simple to perform. It is not, however, suitable for producing a disinfecting agent of a high bactericidal activity at a high rate.

The technical effect of the claimed invention is that a disinfecting agent with improved bactericidal properties can be produced at a high commercial rate.

The claimed technical effect is attained in a method for producing a disinfecting agent by dissolving quaternary ammonium compounds in water in the presence of an active additive, such as a guanidine; preparing a 1% to 15% guanidine solution in water by agitating it constantly at a temperature of 30° C. to 90° C.; cooling the solution; monitoring precipitation; filtering the solution, at the end of the precipitation process, using a 10 to 1 micron mesh filter; adding quaternary ammonium compounds to the solution; and raising the concentration of the quaternary ammonium compounds in the solution to between 0.1% and 3.0%.

It is desirable to use polyhexamethylene-guanidines as guanidines.

It is also desirable to use bi-guanidine as a guanidine.

It is preferred to use mixtures of alkyl-dimethyl-benzyl-ammonium chloride and quaternary ammonium salts of dimethyl-amine as the quaternary ammonium compounds.

It is also preferred to use mixtures of alkyl-dimethyl-benzyl-ammonium chloride and quaternary salts of tertiary amine as the quaternary ammonium compounds.

In accordance with this invention, polyhexamethylene-guanidines (PHMG) and bi-guanidine (trade name Glybutyl) are used as guanidines. It is of some interest to consider using polymer salts—PHMG chloride (Metacid TU-10-09-41-90) and PHMG phosphate (Phogucid TU 031-1-92)—for purifying and disinfecting water. Further, the following quaternary ammonium compounds are also used in this invention: mixtures of alkyl-dimethyl-benzyl-ammonium chloride and quaternary ammonium salts of dimethyl-amine or tertiary amine (Catamine AB-TU-6-01-816-75).

The invention is illustrated in the following examples:

EXAMPLE 1

A 7% solution of polyhexamethylene-guanidine hydrophosphate is prepared in 100 kg of water as the solution is agitated constantly by a pump at a temperature of 60° C. The solution is then cooled and precipitation is monitored, and once precipitation is completed, the solution is filtered through a 5 micron mesh filter, whereupon a mixture of alkyl-dimethyl-benzyl-ammonium chloride and quaternary ammonium salts of dimethyl-amine is added to the solution, and the concentration of the mixture in the solution is brought to 1.5%. The efficiency of the method is measured from the time needed to produce the disinfecting agent. The disinfecting efficiency of the disinfecting agent is measured by a conventional technique, which includes measuring the optimal dose of the disinfecting agent required to reach a minimum microbe count and a minimum level of the coli index. The technique used to measure the total microbe count in water comprises measuring the total number of mesophilous, mesotropic, and facultative aerobes capable of growing on nutrient agar in 1 $cm^3$ at a temperature of 37° C. during 24 hours, producing colonies visible under 2 to 5 magnification.

EXAMPLE 2

A 1% solution of polyhexamethylene-guanidine hydrochloride is prepared in 100 kg of water as the solution is agitated constantly in the same manner and at the same intensity as in Example 1 at a temperature of 30° C. The solution is then cooled and precipitation is monitored, and once precipitation is completed, the solution is filtered through a 10 micron mesh filter, whereupon a mixture of alkyl-dimethyl-benzyl-ammonium chloride and quaternary ammonium salts of dimethyl-amine is added to the solution, and the concentration of the mixture in the solution is brought to 0.1%. The efficiency of the method and disinfecting agent is measured as in Example 1.

EXAMPLE 3

A 15% solution of biguanidine is prepared in 1 kg of water as the solution is agitated constantly in the same manner and at the same intensity as in Example 1 at a temperature of 90° C. The solution is then cooled and precipitation is monitored, and once precipitation is completed, the solution is filtered through a 1 micron mesh filter, whereupon a mixture of alkyl-dimethyl-benzyl-ammonium chloride and quaternary ammonium salts of tertiary amine is added to the solution, and the concentration of the mixture in the solution is brought to 3.0%. The efficiency of the method and disinfecting agent is measured as in Example 1.

EXAMPLE 4

A 0.2% solution of biguanidine is prepared in 100 kg of water as the solution is agitated constantly in the same manner and at the same intensity as in Example 1 at a temperature of 95° C. The solution is then cooled and precipitation is monitored, and once precipitation is completed, the solution is filtered through a 0.5 micron mesh filter, whereupon a mixture of alkyl-dimethyl-benzyl-ammonium chloride and quaternary ammonium salts of dimethyl-amine is added to the solution, and the concentration of the mixture in the solution is brought to 0.02%. The efficiency of the method and disinfecting agent is measured as in Example 1.

EXAMPLE 5

A 20% solution of polyhexamethylene-guanidine hydrochloride is prepared in 100 kg of water as the solution is agitated constantly in the same manner and at the same intensity as in Example 1 at a temperature of 25° C. Precipitation is monitored, and once precipitation is completed, the solution is filtered through a 15 micron mesh filter, whereupon a mixture of alkyl-dimethyl-benzyl-ammonium chloride and quaternary ammonium salts of tertiary amine is added to the solution, and the concentration of the mixture in the solution is brought to 4.0%. The efficiency of the method and disinfecting agent is measured as in Example 1.

The preparation time and efficiency of the disinfecting agent prepared by the claimed method in comparison with the disinfecting agent prepared by a prior art method are shown in Table 1.

TABLE 1

| Readings | | Agent of example: | | | | | Prior art agent |
|---|---|---|---|---|---|---|---|
| | | 1 | 2 | 3 | 4 | 5 | |
| Total agent preparation time, minutes | | 60 | 75 | 75 | 90 | 90 | 100 |
| Minimum dose, mg/liter, for microbe count of 50 col./ml, or less | Fall (November) | 2.0 | 2.0 | 2.0 | 3.0 | 3.0 | 3.0 |
| | Winter (December) | 3.0 | 3.0 | 3.0 | 4.0 | 4.0 | 4.0 |
| Coli index | | | | None | | | |

As follows from the Table, the microbe count and coli index are reduced to the levels of microbiological standards in fall (November) required under Sanitary Regulations 2.1.4.559-96, "Drinking Water: Hygienic Standards of Water Quality in Centralized Water Supply Systems. Quality Monitoring," at a rate of 2 mg/liter of the claimed disinfecting agent (with microbe count of, or under, 50 and zero coli index). Disinfection of water drawn from rivers in wintertime (December) is observed at an agent dose of 3 mg/liter, while the agent prepared by the prior art method is used in doses of 3 and 4 mg/liter to achieve similar results. Besides, the preparation time of the disinfecting agent produced by the claimed method is 30% to 50% shorter.

To sum up, the method for producing a disinfecting agent by dissolving quaternary ammonium compounds, for example, a mixture of alkyl-dimethyl-benzyl-ammonium chloride and quaternary ammonium salts of dimethyl-amine or quaternary ammonium salts of tertiary amine in water in the presence of an active additive, such as a guanidine, for example, bi-guanidine or polyhexamethylene guanidine, which are used to prepare a 1% to 15% solution in water, as the solution is agitated constantly at a temperature within the range of 30° C. to 90° C., the solution is cooled, and precipitation is monitored, and once the precipitation is completed, the solution is filtered using a 10 to 1 micron mesh filter, whereupon quaternary ammonium compounds are added to the solution, and their concentration is brought to between 0.1% and 3.0%, makes it possible to raise the efficiency of the process by 50% to 100%, and simultaneously to improve the bactericidal activity of the disinfecting agent, expand the range of applications thereof, and lower its production costs.

What is claimed is:

1. A method for producing a disinfecting agent comprising:
   preparing a 1% to 15% solution of a guanidine in water by agitating the solution constantly at a temperature within the range of 30° C. to 90° C.;
   followed by cooling the solution and monitoring precipitation;
   followed by filtering the solution upon completion of the precipitation process using a 1-10 micron mesh filter;
   followed by adding quaternary ammonium compounds to the solution; and then
   bringing concentration of quaternary ammonium compounds in the solution to between 0.1% and 3.0%.

2. The method of claim 1, wherein bi-guanidine is used as the guanidine.

3. The method of claim 1, wherein a polyhexamethylene guanidine is used as the guanidine.

4. The method of claim 1, wherein a mixture of alkyl-dimethyl-benzyl-ammonium chloride and quaternary ammonium salts of dimethyl amine is used as the quaternary ammonium compounds.

5. The method of claim 1, wherein a mixture of alkyl-dimethyl-benzyl-ammonium chloride and quaternary ammonium salts of tertiary amine is used as the quaternary ammonium compounds.

* * * * *

UNITED STATES PATENT AND TRADEMARK OFFICE
CERTIFICATE OF CORRECTION

PATENT NO.         : 8,431,616 B2  
APPLICATION NO. : 12/084594  
DATED              : April 30, 2013  
INVENTOR(S)      : Balekhov et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1239 days.

Signed and Sealed this
Eighth Day of September, 2015

Michelle K. Lee
*Director of the United States Patent and Trademark Office*